(12) United States Patent
Strauss (10) Patent No.: US 6,543,247 B2
(45) Date of Patent: Apr. 8, 2003

(54) WAIST-MOUNTED EVAPORATIVE PERSONAL COOLER

(76) Inventor: Ted Strauss, 144 Toyon Dr., Fairfax, CA (US) 94930

(*) Notice: Subject to any disclaimer, the term of this patent is extended or adjusted under 35 U.S.C. 154(b) by 77 days.

(21) Appl. No.: 09/825,666

(22) Filed: Apr. 3, 2001

(65) Prior Publication Data

US 2002/0170309 A1 Nov. 21, 2002

Related U.S. Application Data (60) Provisional application No. 60/194,223, filed on Apr. 3, 2000.

(51) Int. Cl.[7] ............................................. F25D 23/12
(52) U.S. Cl. ...................... 62/259.3; 62/259.4; 261/116
(58) Field of Search ............................ 62/259.3, 259.4, 62/304, 314; 261/116

(56) References Cited

U.S. PATENT DOCUMENTS

| | | | | |
|---|---|---|---|---|
| 4,691,762 A | * | 9/1987 | Elkins et al. ................. 165/46 |
| 5,046,329 A | * | 9/1991 | Travis, III .................. 62/259.3 |
| 5,217,408 A | * | 6/1993 | Kaine ........................... 454/338 |
| 5,363,663 A | * | 11/1994 | Chen ............................. 62/99 |
| 5,386,823 A | * | 2/1995 | Chen ..................... 128/204.15 |
| 5,438,707 A | * | 8/1995 | Horn ............................. 2/457 |
| 5,564,124 A | * | 10/1996 | Elsherif et al. .................. 2/69 |
| 5,968,084 A | * | 10/1999 | Augustine et al. .......... 607/107 |
| 6,192,702 B1 | * | 2/2001 | Shimogori ................ 62/259.3 |
| 6,257,011 B1 | * | 7/2001 | Siman-Tov et al. ........ 62/259.3 |

* cited by examiner

*Primary Examiner*—William E. Tapolcal
*Assistant Examiner*—Mohammad M. Ali (57) ABSTRACT

A waist-mounted evaporative personal cooling device designed to cool the back of a user, comprises a blower (25), a liquid reservoir (29), a means to deliver liquid from the reservoir a mist of droplets into blower-forced air (33) or directly onto the skin area to which the forced air will be directed (45), and a duct (27) to guide forced air under the user's shirt or blouse and directly onto or across the skin of the user's back. The device improves on prior art coolers by delivering a powerful evaporative cooling effect directly to a user's back, while being compact, comfortably wearable, and requiring the user to do little or nothing to get its benefit.

40 Claims, 6 Drawing Sheets

WAIST-MOUNTED EVAPORATIVE PERSONAL COOLER

CROSS-REFERENCE TO RELATED APPLICATIONS

This application claims benefit of provisional application serial No. 60/194,223, filed Apr. 3, 2000.

BACKGROUND

1. Field of Invention

This invention relates to the field of personal comfort devices, specifically to evaporative personal cooling devices.

2. Prior Art

Throughout history, people have used various methods to keep themselves cool on hot days and in hot environments, especially when engaged in strenuous activities. Simple methods of personal cooling include wearing a moistened bandanna around one's neck, shading oneself with a hat or parasol, fanning oneself, and using portable misting devices. All of these have at least one of the following disadvantages:

- They require the user to hold a device or to do something to get its benefit (which is not only bothersome, but such activity can generate more heat and exhaustion)
- They wet the user's clothing
- They provide only short-term relief
- They provide relatively poor cooling power U.S. Pat. No. 5,802,8 of Ted N. Strauss (granted Sep. 8, 1998) shows a cooler that uses a wind-chill effect within the device and delivers the resulting coolness to the skin of the user without requiring the user to hold anything or to get wet. However, this device is not as affordable as would be desirable, creates a bothersome humming noise close to the ears, and makes a questionable fashion statement.

With the development of modern technologies, new ways have been found to produce a cooling effect. Some systems have employed elaborate mechanisms for pumping cool gels or fluids through a shirt or vest; others are essentially portable freon-type refrigerators, still others transfer coolness from a refrigerator or freezer to the body over time via phase-change substances. Some have proposed the use of compressed gas to create a stream of moving air across the skin. Peltier cells have also been explored for use in personal cooling devices. Still, each of these methods has serious drawbacks for the average user due to cost, complexity, and/or lack of effectiveness over time.

More recently, Misty Mate, Inc., of Gilbert, Ariz., has introduced a device under the trademark Arctic Blast. This device is strapped to the front of a user's body, and blows air and a water mist up the front of the user's body. This approach has several major disadvantages: 1) it wets the user's shirt, 2) because it blows over the user's shirt, it either doesn't cool the user's torso or requires the user to remove his or her shirt to receive its benefit, 3) it destroys the user's hairdo, and 4) it is bulky, unattractive, and relatively expensive.

OBJECTS AND ADVANTAGES

Several objects and advantages of this invention are to provide an improved portable cooling device which . . .

- Delivers significant evaporative cooling directly to the skin of the user's back
- Does not require the user to hold it
- Requires the user to do little or nothing to get its benefit
- Can be comfortably worn on a user's body
- Is attractive and easily affordable Other objects are to provide and inexpensive, unobtrusive, lightweight, hands-free, powerful, wearable evaporative cooler. Further objects and advantages will become apparent from a consideration of the drawings and ensuing description.

SUMMARY

A waist-mounted evaporative personal cooling device consists of a blower or other means to move air, a water reservoir, a means to inject water from the reservoir as a mist of droplets into the moving air, and a housing designed to guide the fan-forced air and injected mist under the user's shirt or blouse and directly onto the skin of the user's back.

REFERENCE NUMERALS

| | | |
|---|---|---|
| 18 Housing | 28 Fill cap | 38 Shirt edge concealer |
| 19 Fannypack-type belt | 29 Water reservoir | 39 Strap handles |
| 20 Belt clasp | 30 Water | 40 Balloon |
| 21 Loose belt end | 31 Air pressure bulb | 41 User's shirt |
| 22 Power switch | 32 Air tube | 42 Electric pump |
| 23 Batteries | 33 Atomizer head | 43 Blower switch |
| 24 Blower motor | 34 Water tube | 44 Pump switch |
| 25 Blower impeller | 35 Fine spray of water | 45 Spray nozzle |
| 26 Intake vents | 36 Drain hole | |
| 27 Exhaust duct | 37 Foam buttons | |

Figure 1:
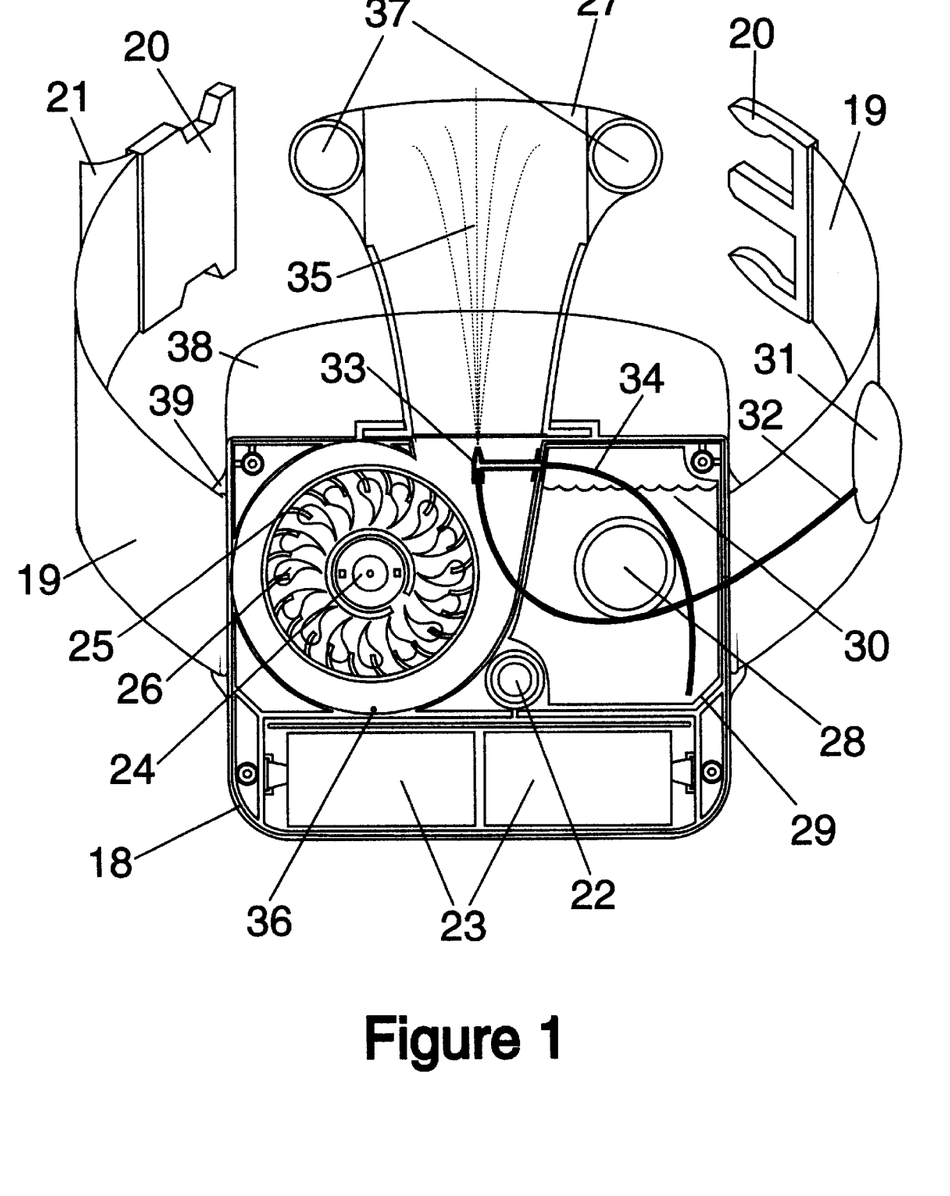
FIG. 1 shows a front transparent view of the preferred embodiment of a personal evaporative cooler according to my invention.
Figure 2:
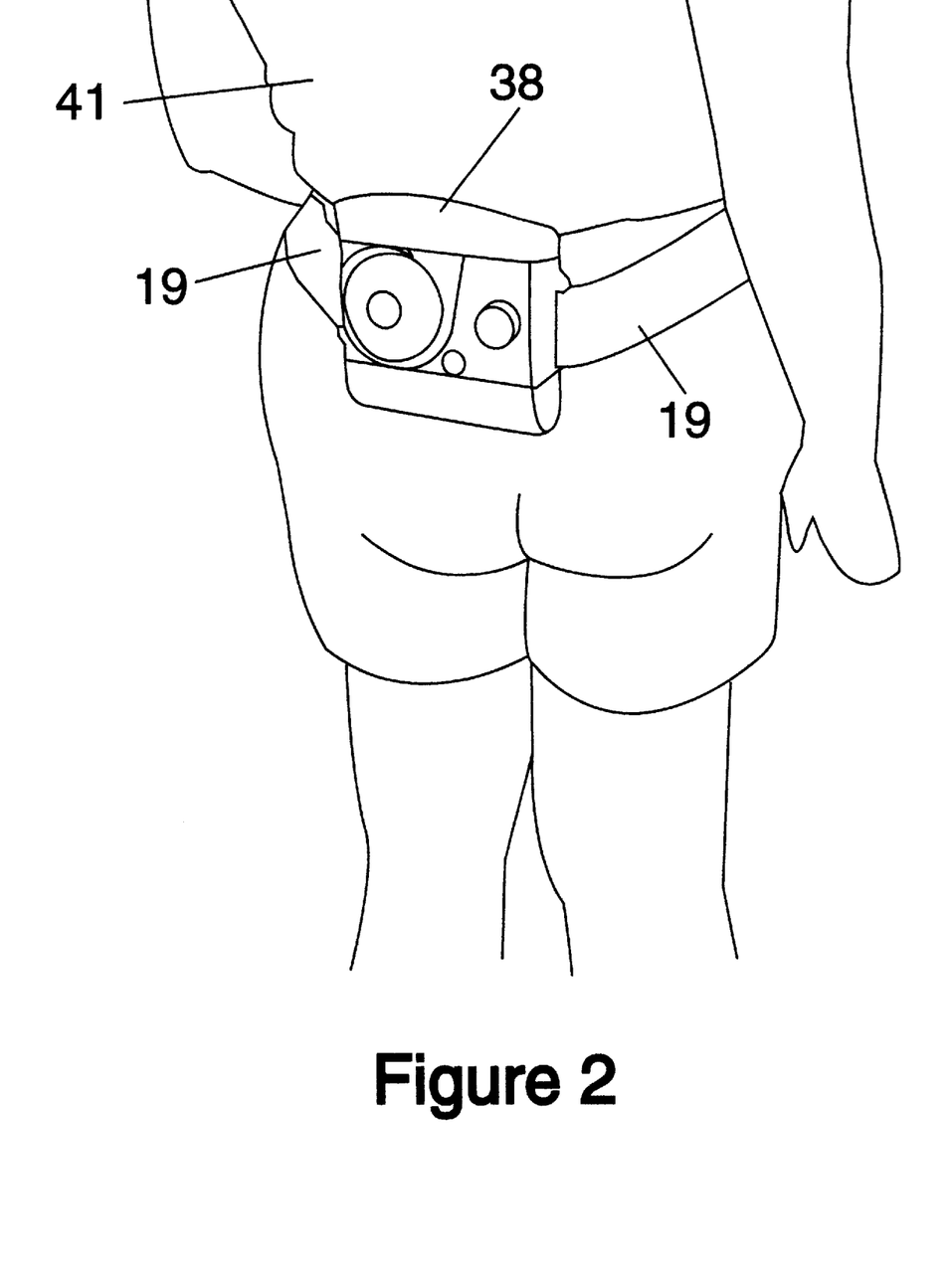
FIG. 2 shows a user wearing the personal portable cooler.
Figure 3:
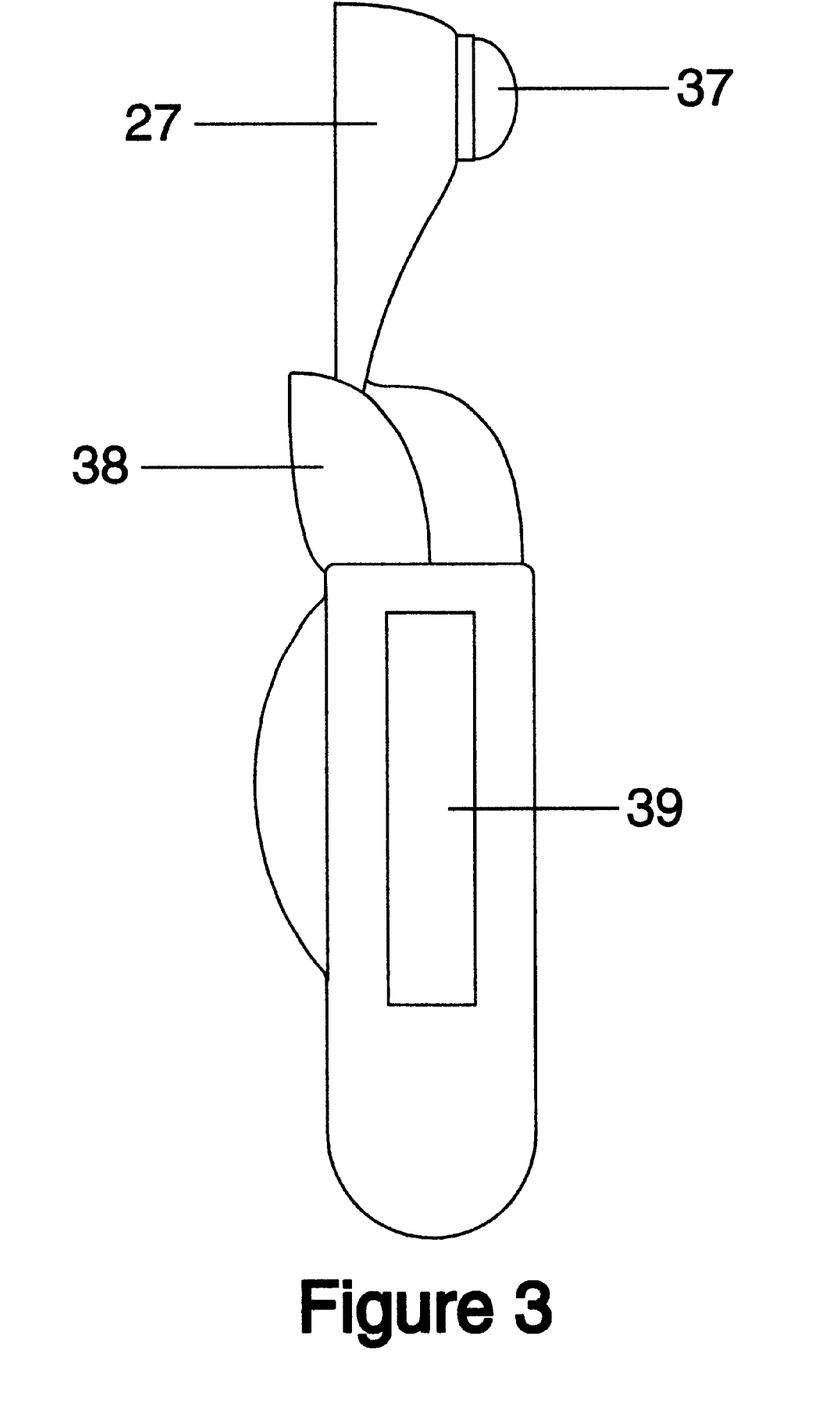
FIG. 3 shows a side view of the personal portable cooler.

DESCRIPTION OF PREFERRED EMBODIMENT (FIGS. 1–3)

The preferred embodiment of the personal portable cooler is illustrated in FIGS. 1, 2 and 3. FIG. 1 is a transparent view, and shows the device as an observer would see it strapped on the back of a user's waist. A housing 18 is preferably molded in a rigid plastic. Fannypack-type belt sections 19 extend from the opposite sides of housing 18 and are preferably made of elastic belting. Belt clasps 20 are used to clip the two ends of belt 19 together at the front of the user's waist. A loose belt end 21 is pulled to tighten belt 19 around the user's waist. A push-on-push-off type power switch 22 is mounted on housing 18 facing outward, and is protected with a rubber boot to prevent water from entering and corroding the internal contacts. Batteries 23 are provided in the bottom of housing 18 and may be standard alkaline "D" cells, but may be of any type that supplies sufficient power to the unit for a reasonable period of time. Such batteries may be removable and rechargeable, or recharged while in the unit.

A small electric motor 24 is mounted inside the housing for spinning a blower impeller 25. Intake vents 26 in the housing are of sufficient size to permit a free flow of air into the area of the blower impeller. An exhaust duct 27 at the top of housing 18 is a concave cowling, open toward the skin of the user's back, with foam buttons 37 (or any other soft material) provided to protect the user's skin from being abraded by the motion of duct 27 against the user's skin while the user is active. A fill cap 28 prevents water 30 from escaping a water reservoir 29. An air pressure bulb 31, mounted on belt 19 toward the front of the user's waist, is preferably made of molded rubber, and may have a one-way valve inserted at the end opposite an air tube 32. An air tube 32, connecting bulb 31 and atomizer head 33, is made of vinyl or any material that is both flexible and durable. Bulb 31 and tube 32 and tube 32 are preferably hidden within belt 19 for aesthetic purposes. Bulb 31 is located toward the front of the user's body for easy access. An atomizer head 33 is preferably molded of rigid plastic and designed much like old-fashioned perfume atomizer heads, utilizing the Venturi principle. A water tube 34, connecting reservoir 29 and atomizer 33, is preferably made of stiff plastic. A drain hole 36 is provided at the bottom of the blower area in housing 18, and is of sufficient diameter to permit any water that may accumulate under the blower impeller to drain out of the housing without being impeded by surface tension effects. Shirt edge concealer 38 is a thin, generally rectangular extension of housing 18 which, if opaque, hides, and, if transparent, neatly arranges the edge of the user's shirt 41 (FIG. 2). Strap handles 39 are used to attach belt sections 19 to housing 18.

Operation of Preferred Embodiment (FIGS. 1–3)

Referring to FIG. 1, housing 18 contains all internal parts and is attachable to the user's waist using belt 19. When power switch 22 is activated, batteries 23 supply power to blower motor 24, which spins impeller 25. As impeller 25 spins (in this view, counterclockwise), it draws ambient air into the device through intake vents located in housing 26 directly facing the inside of impeller 25, and propels the air up and out of the device through exhaust duct 27. Exhaust duct 27 is generally concave, open toward the user's skin. It serves three functions: 1) it guides air upward, 2) it holds the shirt or blouse away from the skin to make a clear opening for the air stream, and 3) it protects the shirt or blouse from being wet by the water spray. As air exits duct 27, it blows across the user's back, cooling the user's skin.

To further assist in cooling, the user may remove fill cap 28 from water reservoir 29 and fill water reservoir 29 with water 30. Whenever extra coolness is desired, the user presses bulb 31. This forces air through tube 32, and into atomizer head 33. As the air moves through head 33, it creates a low pressure area over the top of tube 34, causing water to be drawn up into head 33 and to mix with the air. As the air and water mixture moves through the spray nozzle portion of head 33, it exits as a fine spray 35, which is then carried upward with the air through exhaust duct 27 and onto the user's back. This causes the user's skin to be moistened. As the air moves across the moistened skin, the moisture evaporates, drawing heat away from the user's skin, creating a wind chill effect, cooling the user.

Any water that drips back down into the area of the blower housing can drain out of the housing through drain hole 36. Foam buttons 37 protect the user's back from being uncomfortably abraded by exhaust duct 27. Shirt edge concealer 38 (FIG. 2) hides the untucked edge of the users shirt, keeping the user's appearance neat.

FIG. 2 depicts a user wearing the personal portable cooler. To use the device, the user holds the ends of belt 19 with housing 18 behind the waist and snaps connectors 20 together in front of the waist. Belt 19 will then secure the device to the user's waist. The user then pulls on loose belt end 21 (in this case, on the left side) until the device is comfortably snug against the waist. The user then untucks the back of his or her shirt and pulls the untucked edge over duct 27 and down between duct 27 and concealer 38. Concealer 38 conceals the edge of the user's shirt 41, while exhaust duct 27 is completely hidden by the user's shirt.

FIG. 3 shows a side view of the cooler. Here, shirt edge concealer 38 is clearly seen, along with a space for the edge of the user's shirt between shirt edge concealer 38 and exhaust duct 27. Foam buttons 37 are also visible in this view. Strap handles 39 show where belt 19 is attached.

Figure 4:
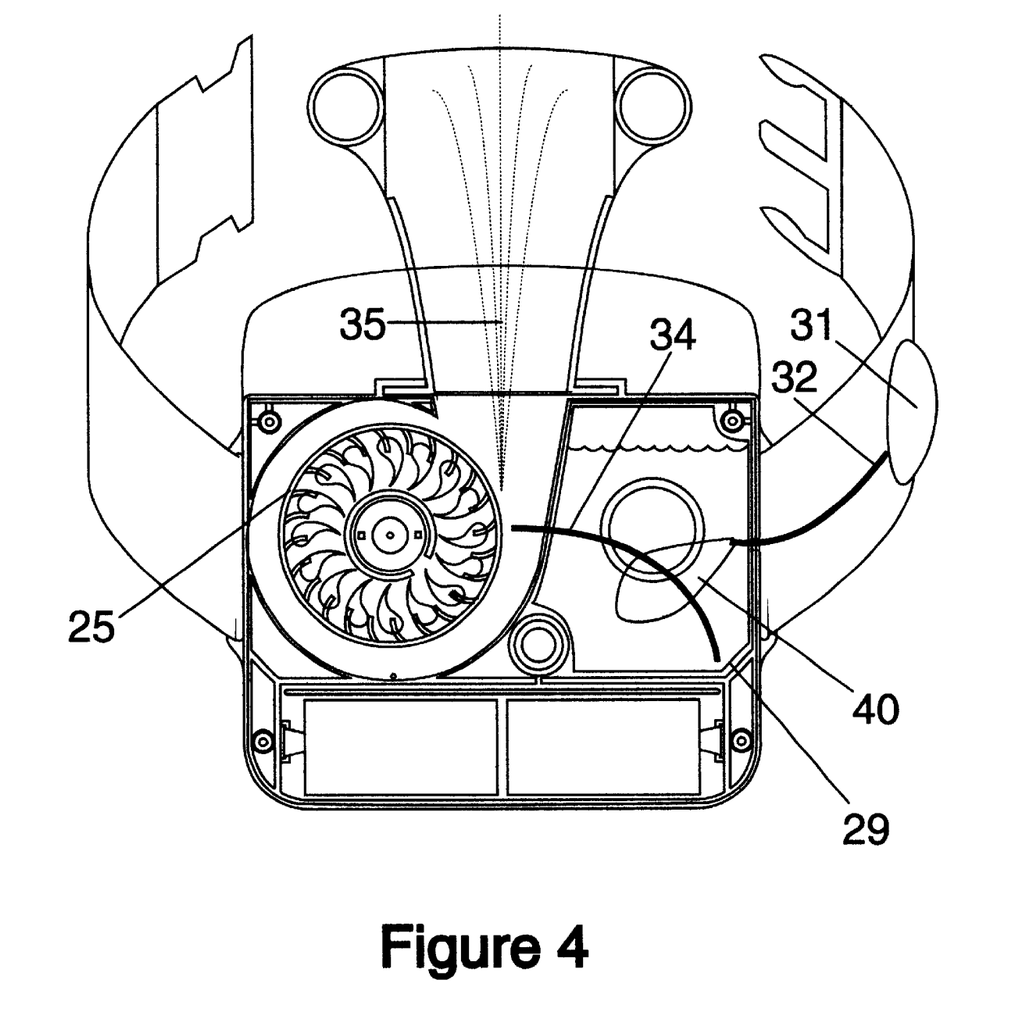
FIG. 4 shows a front transparent view of a first alternative embodiment of the cooler.

Description of First Alternative Embodiment (FIG. 4)

In a first alternative embodiment, pictured in FIG. 4, tube 34 extends from reservoir 29 into the air passageway surrounding impeller 25 and directs water at impeller 25. A balloon 40 is inside of reservoir 29 at the end of tube 32.

Operation of First Alternative Embodiment (FIG. 4)

When the user presses bulb 31, air is forced through tube 32, which partly inflates balloon 40. As balloon 40 expands, pressure is transmitted into reservoir 29, causing water to move through tube 34, propelling it into blower impeller 25. This breaks the water stream into tiny droplets, which in turn are propelled with the upward moving air through exhaust duct 27 and onto the user's skin.

Balloon 40 is also used to prevent water in reservoir 29 from backing into air tube 32. In a variation on this approach, a spray nozzle is provided at the blower end of tube 34. This atomizes the water before it hits the impeller, breaking the spray into even finer droplets.

In a related approach, balloon 40 can be eliminated by incorporating a one-way or check valve into bulb 31 so that air can only move from bulb 31 toward water reservoir 29, and not in the reverse direction.

In another variation, the blower impeller has a narrow ring of small plastic fingers extending radially from the blade centers. These fingers can be of sufficient number to break the water into even smaller droplets. In this approach, drain hole 36 can be eliminated, as any water accumulating under the blower impeller would be picked up by the fingers and flung out with the moving air. An advantage of this approach is that the water spray can be finer and more copious. However, as the batteries wear down, the spray is less useful.

Figure 5:
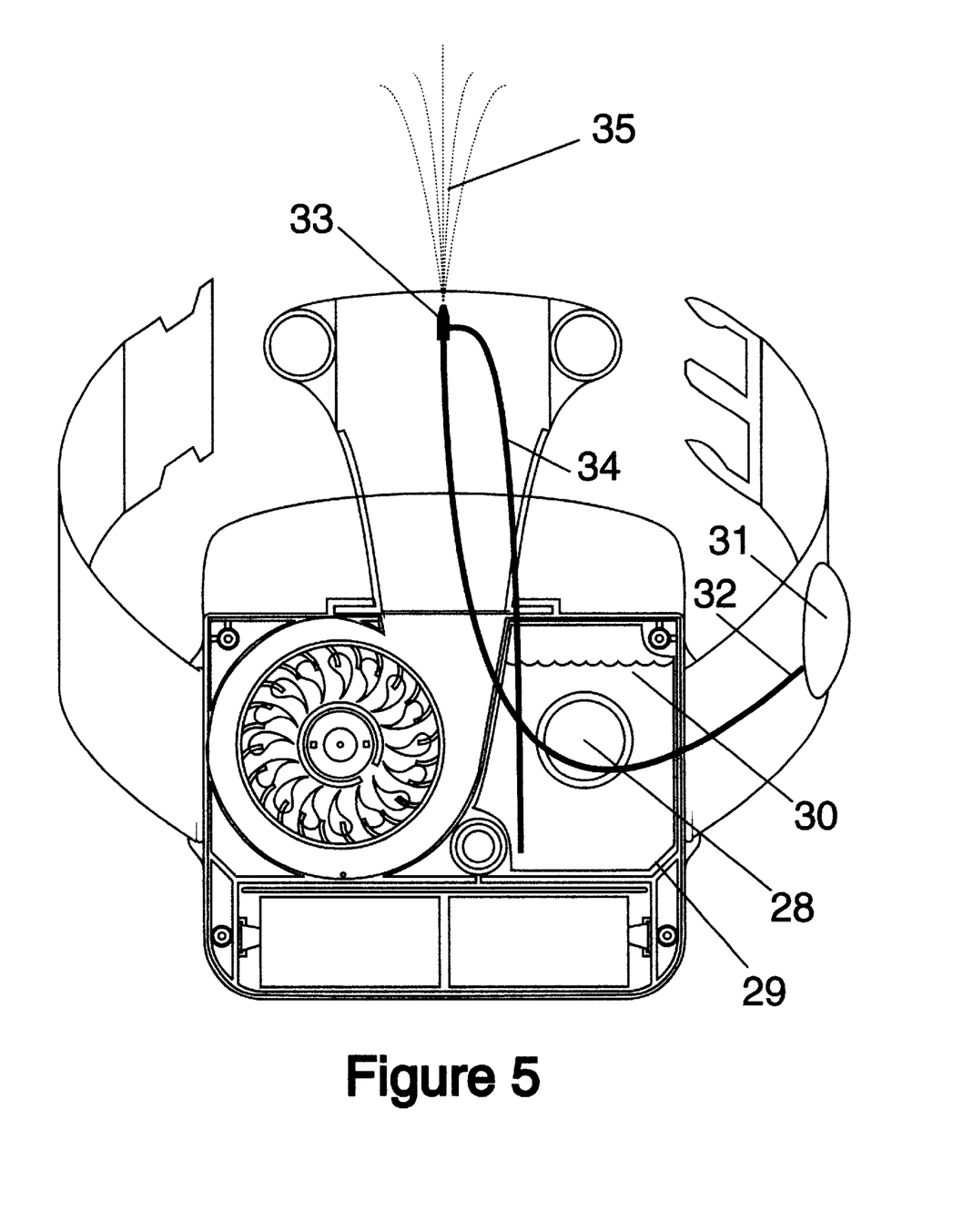
FIG. 5 shows a front transparent view of a second alternative embodiment of the cooler.

Description of Second Alternative Embodiment (FIG. 5)

In a second alternative embodiment, pictured in FIG. 5, atomizer head 33 is positioned at a location partway up the user's back, avoiding reliance on the blower-forced air to deliver spray 35 to the user's back. A Venturi-type atomizer is shown, but any of several alternative devices may be used to create the water spray.

Operation of Second Alternative Embodiment (FIG. 5)

In this embodiment, when the user presses bulb 31, air in tube 32 is forced into atomizer 33, which dispenses spray 35 directly to the skin of the user's back. An advantage of this approach is that none of the water is wasted accumulating on the inside of exhaust duct 27. Another advantage is that as the batteries wear down and the stream of forced air becomes less powerful, the spray still reliably reaches the point or points on the user's skin that are found to be most useful.

Figure 6A:
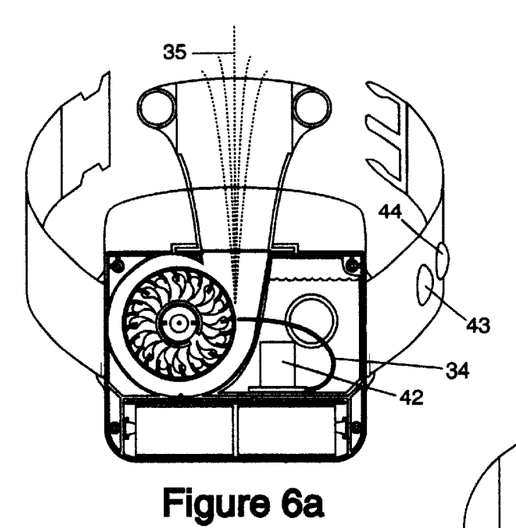
FIGS. 6a-c show a front transparent view of a third alternative embodiment of the cooler.
Figure 6B:
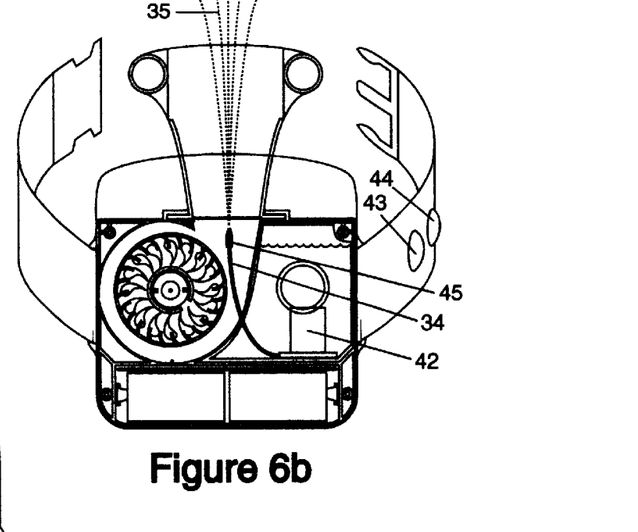
Figure 6C:
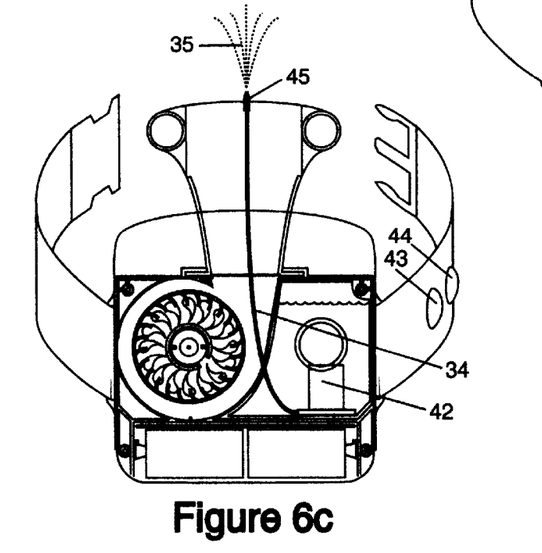

Description of Third to Fifth Alternative Embodiments (FIGS. 6a-c)

This group of alternative embodiments makes use of a small electric pump 42 to move water, enabling automated delivery of the water spray. Pump 42 may be of any variety, such as centrifugal, peristaltic, diaphragm, piston, etc. All of these variations use a blower switch 43 to turn on blower motor 24 and a momentary contact switch 44 to activate electric pump 42.

Operation of Third to Fifth Alternative Embodiments (FIGS. 6a-c)

FIG. 6a depicts the use of electric pump 42 to propel water toward impeller 25 to create a spray, in similar manner as shown in FIG. 4. FIG. 6b depicts the use of electric pump 42 to force water through a fine spray nozzle 45 to create a spray that is delivered to the user's skin by mixing it with the blower-forced air. FIG. 6c shows the use of electric pump 42 to force water through a fine spray nozzle 45 to create a spray that is delivered directly to the user's skin without relying on the forced air. In FIGS. 6b and 6c, the pump can be used to force air through a Venturi-type atomizing nozzle as in FIG. 1 instead of propelling the water directly. In variations not depicted, the Venturi-induced or forced water spray can be directed at the blower impeller, further breaking the spray into smaller droplets.

An advantage of this group of embodiments is that the delivery of the water spray can be electro-mechanically or electronically automated. For example, a brief spray can automatically be generated every few seconds, the number of seconds varying according to where the user sets a potentiometer, or whether the user sets a switch to one of several different settings.

Conclusion, Ramifications, and Scope

From the above descriptions and drawings, it can be seen that my personal portable cooler clearly improves on prior art cooling devices. It offers a highly effective evaporative personal cooling system that delivers cooling power directly to the skin of the user's back by guiding a powerful stream of air along with a mist of water under the user's shirt or blouse. My cooler also is compact, lightweight, and physically attractive, and includes means to keep the user's appearance neat.

Many variations on the embodiments described above can be employed within the intended scope of the invention, as described below.

Water spray can be created by a controlled drip of water onto the inside or outside of the blower impeller. Such drip action can be left uncontrolled, or can be controlled by manually opening or closing a valve, or by using an electromechanical means such as an electric valve, or a nitinol wire wrapped around the water tube. In one variation, the dripping water can, instead of dripping directly onto the blower impeller, drip onto a brush that is in continuous contact with the blower impeller. In another variation, the water drips onto a brush and the user hits a lever that pops the brush tip into blower wheel to create the spray. In all variations using a brush, some other absorbent material can be used. In fact, the absorbent material itself could be used as the water reservoir, with mist being created by touching the absorbent material or an abutting brush or wicking material to the blower wheel.

In another approach, water (controlled or uncontrolled as above) can drip onto an open mesh, where droplets naturally collect at the mesh intersections. As forced air from the blower moves through the mesh, it propels the droplets into the moving air. This approach, however, requires a very strong blower to work properly.

Trigger and pump-action sprayers, such as are commonly used to dispense household cleaning liquids and perfumes, are obvious candidates for the creation of the water spray. To activate such a mechanism from the belt, a means such as a manually pulled cable or electrically activated nitinol wire (which contracts when heated) can be employed. In all such variations, the mist can be directed at the blower impeller, inside the moving air stream, or at the skin to be cooled.

In another approach, an arm with a weak spring for returning it to its original position can be provided adjacent to the water reservoir that flings a small spoon or brush of water toward the blower impeller. The user can hit a lever which flicks the arm. Similarly, a motor can be used to spin a gear through a water reservoir, flinging droplets of water toward the impeller. A motor can also drive a notched timing belt to throw droplets of water toward the impeller. Or, a motor can pull an arm with a spoon or brush at the end, flinging drops at the blower impeller; elastic can pull the brush or spoon back to its starting position.

Instead of using a motor, a solenoid can be used in many ways. It can push a bladder or piston to cause air or water to move into a spray nozzle or Venturi-type atomizer head. A solenoid can push a bladder that spurts water into the blower impeller. Or, it can be used to move a small spoon or brush loaded with water toward the blower impeller.

In another variation, the forced air from the blower is used to take advantage of the Venturi effect. By channeling some of the moving air into a funnel, sufficient velocity is created to lower the pressure over the top of a water tube, drawing water into a spray nozzle. This approach negates the need for an air pressure bulb, but requires the use of a valve in the water tube that can be manually or electromechanically opened to permit the water to flow into the atomizer head.

Pressurized air or gas can also be used in a variety of ways to create the water spray. It can be used to force water into the blower impeller, to draw water (by the Venturi effect) into an atomizer head, or to force water through a spray nozzle either into the impeller, the air above the impeller, or onto the skin directly. Such pressurized air or gas may be created by manual pumping action or may come from a disposable cartridge (such as a $CO_2$ cartridge) or refillable canister. A water or air pump may also be driven by wind-up spring power, compressed air or gas, or other mechanical means generated by the user.

In another series of embodiments, the same motor used for the blower can be used to move the water. The rotational energy of the motor axle or of the impeller can be harnessed either directly or through a manually or electromechanically-engaged clutch to drive a pump, timing belt, or other means as described above.

Mechanical means of creating an intermittent spray of water can be used, such as winding up a clock spring that turns a cam, which intermittently triggers the spray mechanism.

Water is not the only liquid that can be used in the portable cooler. Alcohol evaporates more readily, but the fumes may intoxicate the user. Similarly, acetone or other volatile solvents can be used, but would likely have adverse health effects. Additives to water may be employed, including alcohol, scents, oils, or fragrances.

Other means of attaching the device to the user's waist can be employed, such as clipping it to an existing belt. The housing can also have a part that hooks over the waistband of the user's pants or skirt. Although it would be less comfortable and convenient, the device can be suspended from a shoulder strap or designed to be worn as a knapsack.

The blower switch or the pressure button or electric switch which activates the water mist may be on the housing, activated by a remote control unit, or separate from the housing or the belt, but connected by a wire or air hose for use in the user's pocket or clipped to a convenient place on the user's clothing.

Differently shaped or multiple air exhaust extensions can be used to guide forced air to different parts of the body.

Such extensions may also incorporate one or more spray heads to deliver water directly to the various body parts such air is directed toward.

A "power on" indicator, such as an LED, can be provided. A useful addition is also a "low battery" indicator. For example, a two-color LED can indicate "power on," but switch to red when the batteries are low. A "low water" indicator can be used, either visual (such as an LED) or auditory (such as a beep). A low-medium-high or variable power switch can be useful for varying fan speed according to the user's need.

Very different configurations of the portable cooler would result from the use of different types of fan or blower impellers, including radial, axial, and tangential. These approaches, however, tend to be less efficient for the space constraints. Multiple fans and/or blowers can be employed in the device, as well as multiple atomizer or spray mechanisms.

The device may incorporate solar cells for the purpose of directly running the device, supplementing the battery power, or for recharging the batteries. To date, however, solar cells are too inefficient to make such approaches worth incorporating.

The fan or blower impeller need not be driven by electric power; other options include compressed gas (such as a $CO_2$ cartridge), wind-up spring power, manual pump-activated compressed air (such as used for pellet guns), and other mechanical means that take advantage of the user's physical movements. Electrostatic means of creating a stream of forced air may also be used, although such means to date are not sufficiently powerful or efficient for use in a battery-operated device.

The device may vary in size, shape, color, and design, and still fall within the intended scope of the invention. The elements may be put in different positions, i.e., the batteries can be where the water reservoir is depicted, and the water can be where the batteries are shown. Thus, the scope of the invention should be determined by the appended claims and their legal equivalents, rather than by the examples given.

I claim:

1. A device for personal cooling, comprising:
   (a) a housing,
   (b) a liquid reservoir in said housing,
   (c) an air mover in said housing for creating a stream of air,
   (d) a conduit for conveying liquid from said reservoir into said stream of air,
   (e) a duct coupled to said stream of air for directing said air stream out of said housing and onto or across a user's back, and
   (f) a belt for attaching said housing to said user's waist, whereby said user's back is cooled by the combination of said liquid and said stream of air.

2. The device of claim 1 wherein said air mover is a fan or blower having a spinning impeller and said conduit for conveying liquid includes a liquid atomizing means.

3. The device of claim 2 wherein said liquid atomizing means is a Venturi-type atomizer.

4. The device of claim 2 wherein said liquid atomizing means is a spray nozzle.

5. The device of claim 2 wherein said liquid atomizing means comprises means for guiding said liquid into the spinning impeller of said fan or blower.

6. The device of claim 2 wherein said liquid atomizing means comprises an arm or lever, a piston, a tube, and a fine nozzle, said piston being arranged to force said liquid through said tube and out said nozzle at sufficient pressure to create a spray or fine mist.

7. The device of claim 2 wherein said liquid atomizing means comprises a liquid-soaked device which contacts said spinning impeller of said fan or blower.

8. The device of claim 1, further including an electric pump for delivering said liquid into said air stream.

9. The device of claim 8, further including an atomizer and wherein said electric pump is arranged to move said liquid through said atomizer.

10. The device of claim 8, further including a timer circuit for automatically controlling said electric pump.

11. The device of claim 1 wherein said duct comprises a concave cowling, open toward said user's skin, for guiding said forced air under said user's shirt or blouse.

12. The device of claim 11 wherein said duct includes means for holding said user's shirt away from said user's back to provide a free passage for said stream of air to flow upon said users back.

13. A device for personal cooling, comprising:
   (a) a housing,
   (b) a liquid reservoir in said housing,
   (c) a conduit for delivering said liquid onto a user's back,
   (d) an air mover in said housing for creating a stream of air,
   (e) a duct coupled to said air mover for directing said air stream out of said housing and onto or across a user's back, and
   (f) a belt for attaching said housing to said user's waist, whereby said user's back is cooled by the combination of said liquid and said stream of air.

14. The device of claim 13 wherein said air mover is a fan or blower and said means for delivering said liquid includes a liquid atomizing means.

15. The device of claim 14 wherein said liquid atomizing means is a Venturi-type atomizer.

16. The device of claim 14 wherein said liquid atomizing means is a spray nozzle.

17. The device of claim 14 wherein said liquid atomizing means comprises means for guiding said liquid into a spinning gear or device that has extensions for disrupting the flow of said liquid.

18. The device of claim 14 wherein said liquid atomizing means arm or lever, a piston, a tube, and a fine nozzle, said piston being arranged to force said liquid through said tube and out said nozzle at sufficient pressure to create a spray or fine mist.

19. The device of claim 13, further including an electric pump for delivering said liquid into said air stream.

20. The device of claim 19, further including an atomizer wherein said electric pump moves said liquid through said atomizer.

21. The device of claim 19, further including a timer circuit for automatically controlling said electric pump.

22. The device of claim 13 wherein said duct comprises a concave cowling, open toward said user's skin, for guiding said forced air under said user's shirt or blouse.

23. The device of claim 22 wherein said duct includes means for holding said user's shirt away from said user's back to provide a free passage for said air stream to flow upon said user's back.

24. A device for personal cooling, comprising:
   (a) a fan or blower with a spinning impeller for creating a stream of air,
   (b) a source of liquid,
   (c) means for delivering liquid from said source as a mist of droplets onto a user's back, (d) means for guiding said stream of air under a user's shirt or blouse and directly onto or across the skin of the user's back, and (e) a belt for attaching said housing to said user's waist, whereby said user's back is directly cooled by the combination of said liquid and said stream of air.

25. The device of claim 24 wherein said delivering means comprises means for injecting said mist into said stream of air.

26. The device of claim 25 wherein said mist is created with a Venturi-type atomizer.

27. The device of claim 25 wherein said mist is created with a spray nozzle.

28. The device of claim 25 wherein said mist is created by directing a stream of said liquid into said spinning impeller of said fan or blower.

29. The device of claim 25 wherein said mist is created with an arm or lever, a piston, a tube, and a fine nozzle, said piston being arranged to force said liquid through said tube and out said nozzle at sufficient pressure to create a spray or fine mist.

30. The device of claim 25 wherein said means for delivering comprises a liquid-soaked device in contact with said spinning impeller.

31. The device of claim 25, further including an electric pump for delivering said liquid into said air stream.

32. The device of claim 31, further including an atomizer and wherein said electric pump is arranged to move said liquid through said atomizer.

33. The device of claim 31, further including a timer circuit for automatically controlling said electric pump.

34. The device of claim 24 wherein said delivering means comprises means for directly spraying said mist onto said user's back.

35. The device of claim 34 wherein said means for delivering comprises a Venturi-type atomizer.

36. The device of claim 34 wherein said means for delivering comprises a spray nozzle.

37. The device of claim 34 wherein wherein said means for delivering comprises by directing a stream of said liquid into the spinning impeller of said fan or blower.

38. The device of claim 34 wherein said means for delivering comprises with an arm or lever which moves a piston that forces liquid through a tube and out through a fine nozzle at sufficient pressure to create a spray or fine mist.

39. The device of claim 34 wherein said means for delivering comprises by arranging a liquid-soaked device in contact with said spinning impeller.

40. The device of claim 24 wherein said duct comprises a concave cowling, open toward the user's skin, for guiding said forced air under said user's shirt or blouse, and further including means for holding said user's shirt away from said user's back to provide a free passage for said stream of air to flow upon said user's back.

* * * * *